United States Patent
D'Amico et al.

(10) Patent No.: US 10,386,363 B2
(45) Date of Patent: Aug. 20, 2019

(54) ASSAY

(71) Applicant: IDL BIOTECH AB, Bromma (SE)

(72) Inventors: Ylva D'Amico, Järfälla (SE); Gunnar Magnusson, Upplands Väsby (SE)

(73) Assignee: IDL Biotech AB, Bromma (SE)

( * ) Notice: Subject to any disclaimer, the term of this patent is extended or adjusted under 35 U.S.C. 154(b) by 844 days.

(21) Appl. No.: 14/782,527

(22) PCT Filed: Mar. 28, 2014

(86) PCT No.: PCT/SE2014/050376
§ 371 (c)(1),
(2) Date: Oct. 5, 2015

(87) PCT Pub. No.: WO2014/163557
PCT Pub. Date: Oct. 9, 2014

(65) Prior Publication Data
US 2016/0025718 A1  Jan. 28, 2016

(30) Foreign Application Priority Data

Apr. 5, 2013 (SE) ........................ 1350421

(51) Int. Cl.
*G01N 33/53* (2006.01)
*G01N 33/543* (2006.01)
*G01N 33/574* (2006.01)
*G01N 33/577* (2006.01)

(52) U.S. Cl.
CPC ..... *G01N 33/54306* (2013.01); *G01N 33/577* (2013.01); *G01N 33/57496* (2013.01); *G01N 2333/4742* (2013.01)

(58) Field of Classification Search
None
See application file for complete search history.

(56) References Cited

U.S. PATENT DOCUMENTS

| 6,596,476 B1 * | 7/2003 | Lesniewski | C07K 14/005 435/5 |
| 2005/0221399 A1 | 10/2005 | Nakano et al. | |
| 2007/0122856 A1 * | 5/2007 | Georges | G01N 33/57449 435/7.23 |

FOREIGN PATENT DOCUMENTS

| CN | 1677109 A | 10/2005 |
| WO | 2012/112013 A2 | 8/2012 |

OTHER PUBLICATIONS

Harlow, E. and Lane, D., Antibodies: A Laboratory Manual (1988) Cold Spring Harbor Laboratory Press, Cold Spring Harbor, NY, pp. 23-26 ( (Year: 1988).*
Lederman et al. "A single amino acid substitution in a common African allele of the CD4 molecule ablates binding of the monclonal antibody, OKT4" Mol Immunl. Nov. 1991;28(11):1171-81. (Year: 1991).*

* cited by examiner

*Primary Examiner* — Gary Counts
(74) *Attorney, Agent, or Firm* — Rothwell, Figg, Ernst & Manbeck, P.C.

(57) ABSTRACT

A method is described for the detection of at least two of cytokeratins 8, 18 and 19 in a sample. It is practiced by contacting the sample with a solid phase having a first antibody with specificity for cytokeratin 8, a second antibody with specificity for cytokeratin 18 and, optionally, a third antibody with specificity for a first epitope of cytokeratin 19 bound to it and allowing cytokeratins in the sample to bind to the bound antibodies to form complexes. The complexes are then contacted with a first labelled antibody with specificity for a dimer of cytokeratin 8 and 18 and optionally a second labelled antibody with specificity for a second epitope of cytokeratin 19 and allowing the labelled antibodies to bind to the complexes. The labelled antibodies bound to the complexes are then detected. A method for quantitative determination of soluble fragments of at least two of cytokeratin 8, 18 and 19 in a sample and a kit are also described.

22 Claims, 4 Drawing Sheets

Specification includes a Sequence Listing.

ASSAY

CROSS-REFERENCE OF THE RELATED APPLICATION

The present application is a 35 U.S.C. § 371 National Phase Entry Application of PCT/SE2014/050376, filed 28 Mar. 2014, designating the United States which in turn claims priority to Swedish Application No. 1350421-2, filed 5 Apr. 2013. Both applications are incorporated herein by reference in their entireties.

SUBMISSION OF SEQUENCE LISTING

The present application includes a Sequence Listing in electronic format. The Sequence Listing is entitled 4416102SequenceListing.txt, which was created on 10 Aug. 2018 and is 5 kb in size. The information in the electronic format of the Sequence Listing is incorporated herein by reference in its entirety.

FIELD OF THE INVENTION

The present invention relates to the field of cancer and cancer detection. More specifically, the invention relates to a novel assay for sensitive indication e.g. of tumour cell activity. The methods according to the invention may be useful in the management of patients with carcinomas of epithelial origin, e.g. non-small cell lung carcinoma, and bladder cancer.

BACKGROUND OF THE INVENTION

Cancer is one of the leading causes of death in the industrial world. In order to improve patient care, much effort is currently put into finding additional information related to the prognosis, early indications of treatment response, and disease progression. An interesting tool to this end is the use of cancer biomarkers, i.e. substances which are indicative of the presence of cancer in the body. A biomarker may be a molecule secreted by a tumor or a specific response of the body to the presence of cancer. Ideally, such biomarkers can be assayed in non-invasively collected biofluids like urine, blood or serum.

One area of interest is lung cancer, which is the most common and the most deadly cancer disease worldwide. Lung cancer kills more people than colon, breast, and prostate combined (WHO statistics). Approximately 80-85% of lung cancer patients are of non-small cell histology (NSCLC). Small cell lung cancer (SCLC) comprises about 15-20% of all lung cancer cases. The majority of the patients present with advanced and inoperable disease. Resection remains essentially as the only curative treatment for early stage NSCLC. During the last decade a panel of tumor markers have been investigated for their value in lung cancer. The most common biomarkers found to be of clinical significance in lung cancer were CEA, CYFRA, TPA, TPS and NSE. However, the lack of sensitivity and specificity limits the use of cancer biomarkers for screening and early diagnosis of lung cancer. For the prognostic evaluation and monitoring the course of the disease, the cancer biomarkers appear to be more effective.

All eucaryotic cells have cytoplasmic cytoskeletal structures known as intermediate filaments. The cytoskeletal network is responsible for the mechanical integrity of the cell and it is critical during cellular processes like cell division, motility and cell to cell contacts. At present more than 20 different cytokeratins have been identified, of which cytokeratin 8, 18 and 19 are the most abundant in simple epithelial cells. The cytokeratins are epithelial cell specific and the cytokeratin pattern is usually preserved during the transformation of normal cells into malignant cells.

A solid phase two-site immunoradiometric assay (IRMA) that measures defined epitopes on cytokeratins 8, 18 and 19 is commercially available (IDL Biotech, Bromma Sweden) under the trade mark MonoTotal®. The catcher antibodies, the monoclonal antibodies 6D7 (CK8), 3F3 (CK18) and IDLC4 (CK19), are coated on plastic beads. Polyclonal $^{125}$I-labeled antibodies are used as tracer in the assay. The radioactivity is measured in a gamma counter and is proportional to the concentration of cytokeratin antigen fragments. MonoTotal is a quantitative test designed for patient serum testing. MonoTotal is valuable for diagnosis, prognosis, as a prognostic marker and for monitoring treatment of patients. By following the patient with repeated MonoTotal measurements, the physician can obtain critical information about tumor cell activity. A changed MonoTotal marker level indicates changes in tumor cell activity, and elevated levels pointing to the presence of a tumor. This information is considered particularly important during patient management and follow-up, where a blood sample may contribute to the monitoring of therapy and early detection of tumor recurrence. Approximately 15% of the lung cancer patients are diagnosed when the disease is still restricted to the lungs and early detection is critical to increase the chances of survival. By using MonoTotal the physician can get an indication of the course of the disease, measured in terms of tumor cell activity instead of the more conventional tumor load measurements. MonoTotal can provide the physician with a reliable aid for diagnosis, in establishing prognosis, in treatment monitoring and in patient follow-up.

According to published studies, MonoTotal has been shown to have strong association with clinical response in patients. MonoTotal demonstrates much higher sensitivity compared to Cyfra in lung cancer patients. The overall sensitivity of MonoTotal in the diagnosis of lung cancer, independent of histotype, is about 70-75% at 95% specificity. The sensitivity of non-small cell lung cancer (NSCLC) is higher. MonoTotal correlates well with tumor cell activity and the extent of the disease. Furthermore, MonoTotal predicts disease progression (disease free interval and overall survival) and is an early indicator of relapse during follow up in NSCLC. Changes in MonoTotal often precede detection of relapse by conventional image methods. Response to treatment can be detected within few days since the half-life of cytokeratin proteins in serum are less than one day. MonoTotal is a more sensitive tumor marker for NSCLC than the other cytokeratin markers currently used in routine clinical practice.

Another area of interest is bladder cancer, which is a common cancer in men and women worldwide. More than 70 percent of cases are non-muscle invasive bladder cancers, but many patients progress to muscle invasive bladder cancer or metastatic disease. To improve the prognosis of bladder cancer, employing effective methods for early detection and regular follow-up is vital for the patient.

Non-invasive bladder cancer tests have many potential applications, such as helping to diagnose recurrence, reducing the need for invasive testing, and detecting whether patients fall into a high-risk category. UBC® immunoassays (IDL Biotech) are one type of non-invasive test.

However, despite the methods and assays currently on the market, there is still a need for improved diagnostics tools to capture critical clinical data from patients, avoiding disadvantages related to the use of polyclonal antibodies while enabling efficient detection of early signs of disease and a quick measurement of disease status in patients, for example through serum or urine analysis. It is crucial in this area that products and processes meet high quality standards, and are developed, manufactured, and supplied to the market according to standardized procedures.

SUMMARY OF THE INVENTION

Although the available method for indication of tumour cell activity works quite well, it is dependent on the use of radioactively labelled antibodies which are subject to specific regulations and precautions putting an administrative and practical burden on the user of the method. It further depends on the use of polyclonal antibodies from a specific source, which may lead to supply problems if the source fails to provide the polyclonal antibodies. The present inventors have thus identified a need to develop a method which is not dependent on radioactivity or a specific source of polyclonal antibodies, but at the same time is clinically comparable to the existing method.

According to the present invention, one, two or three antibodies are used immobilized to a solid phase to capture cytokeratin(s) from a liquid sample. Labelled antibodies are subsequently contacted with the solid phase and allowed to bind to the immobilized antibody-cytokeratin complexes and bound antibodies are detected.

Thus, in one aspect the invention relates to a method for detection of at least two cytokeratins selected from the group consisting of cytokeratin 8, 18 and/or 19, and/or soluble fragments thereof, in a sample, comprising the steps contacting said sample with a solid phase having immobilized thereon a first antibody with specificity for cytokeratin 8, and/or a second antibody with specificity for cytokeratin 18 and/or a third antibody having specificity for a first epitope of cytokeratin 19;

allowing cytokeratin and/or soluble fragments thereof in said sample to bind to said first, second and/or third antibodies thereby forming complexes;

contacting said complexes with a first labelled antibody having specificity for a dimer of cytokeratin 8 and 18 and a second labelled antibody having specificity for a second epitope of cytokeratin 19;

allowing said labelled antibodies to bind to said complexes; and detecting said labelled antibodies bound to said complexes.

In a further aspect, the invention relates to a method for quantitative determination of soluble fragments of at least two cytokeratins selected from the group consisting of cytokeratin 8, 18 and 19 in a sample, comprising the method according to the above aspect and further a step of quantitatively correlating the amount of bound first labelled antibody having specificity for a dimer of cytokeratin 8 and 18 and, optionally, a second labelled antibody having specificity for cytokeratin 19 with the amount of soluble fragments of cytokeratins 8, 18 and/or 19.

In a further aspect, the invention relates to a kit of parts for performing the method according to any of the above aspects, said kit comprising a solid phase having immobilized thereon a first antibody having specificity for cytokeratin 8, and/or a second antibody having specificity for cytokeratin 18 and/or a third antibody having specificity for cytokeratin 19; and a first labelled antibody having specificity for a dimer of cytokeratin 8 and 18 and, optionally, a second labelled antibody having specificity for cytokeratin 19, preferably in buffered solution.

Further embodiments of the invention are set out in the detailed description below and in the dependent claims.

SHORT DESCRIPTION OF THE APPENDED DRAWINGS

DETAILED DESCRIPTION OF PREFERRED EMBODIMENTS OF THE INVENTION

Figure 1:
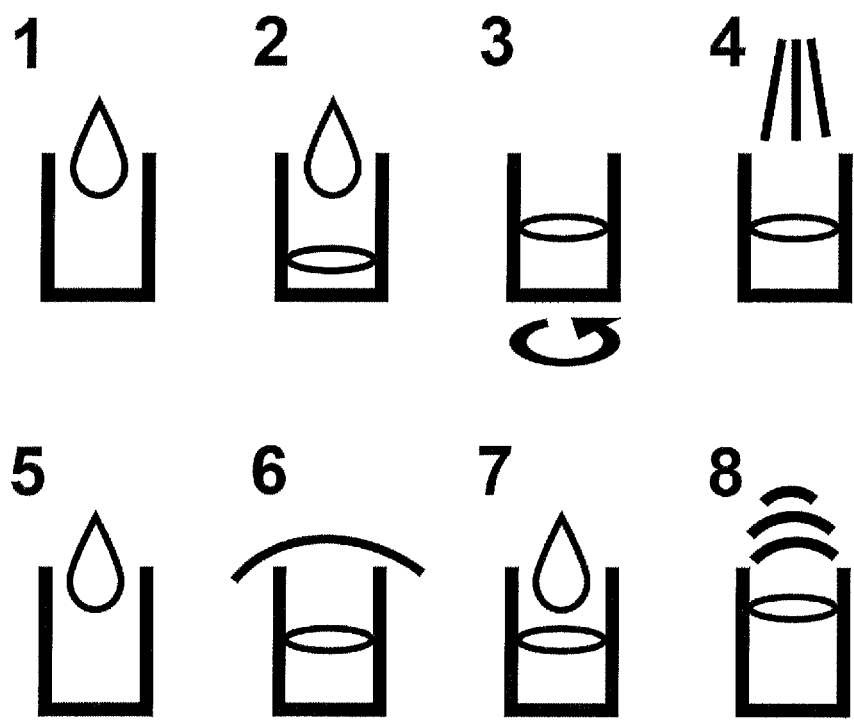
FIG. 1 is a schematic overview of how to perform the method according to the present invention.
Figure 2:
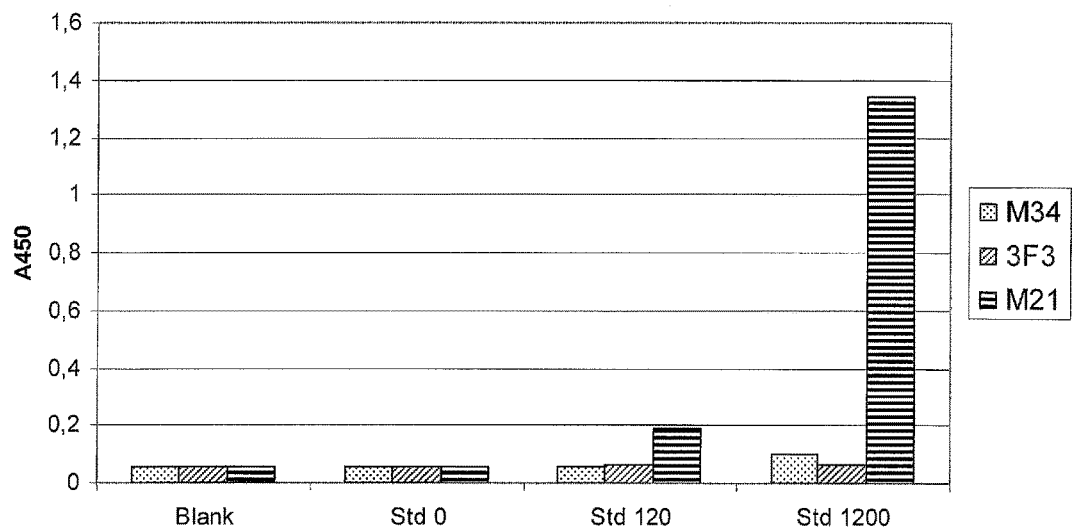
FIGS. 2A-2D show the results obtained in example 2.1.
Figure 2:
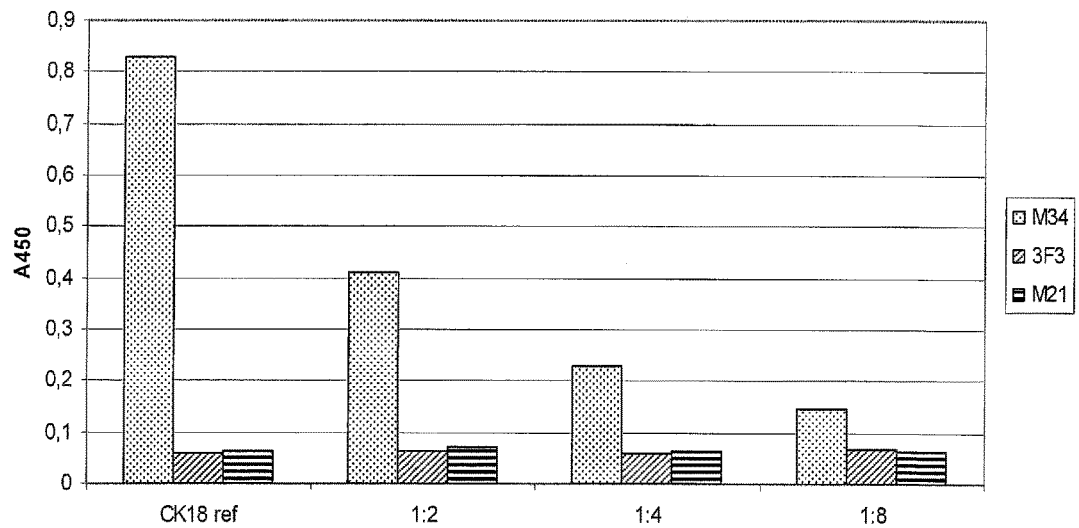
Figure 2:
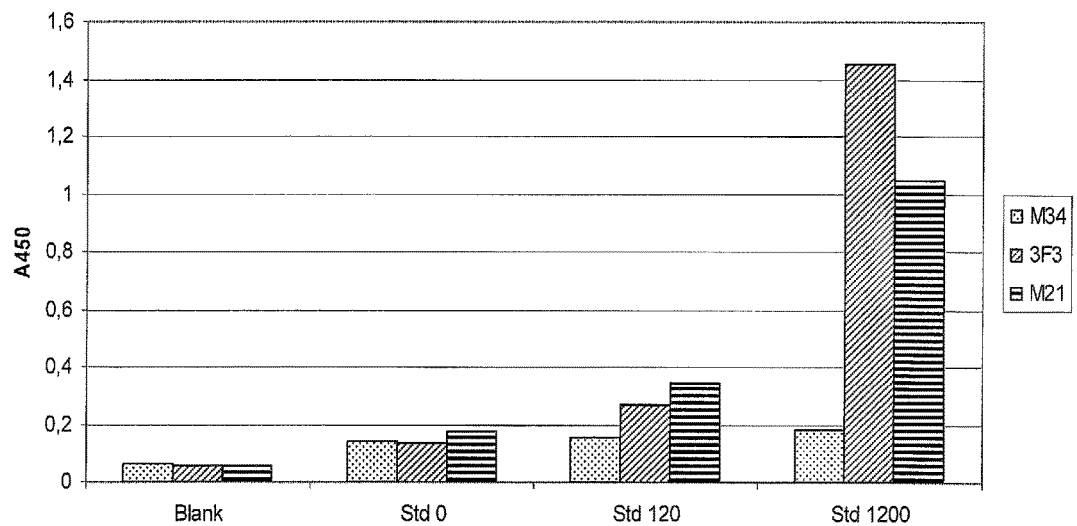
Figure 2:
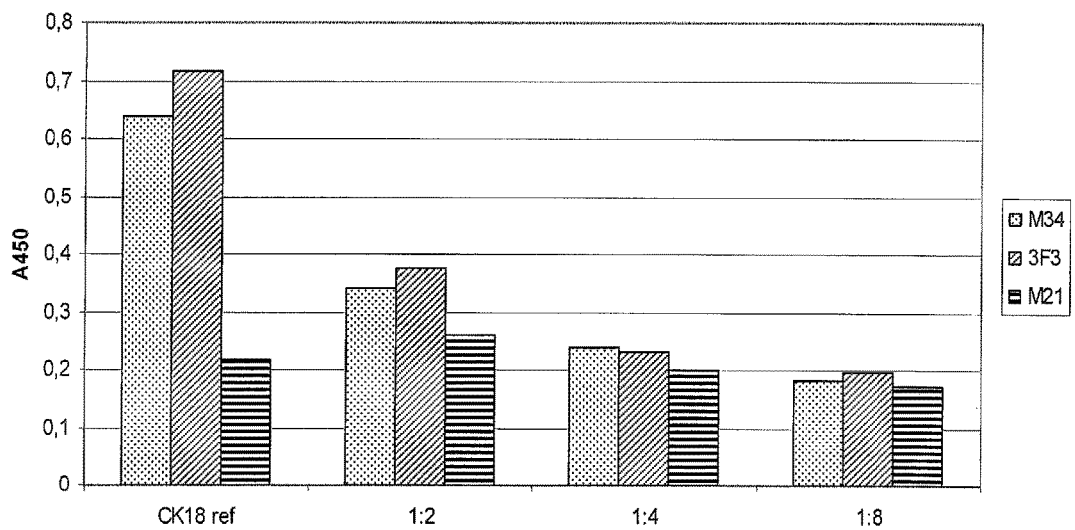

The present inventors have identified a need to produce new or find existing antibodies to facilitate an assay without the drawbacks of prior art technology, while retaining a good clinical correlation with the existing assay, MonoTotal IRMA. In the detailed description below, the term "having affinity for" is used for antibodies which are specific for their respective targets, as will easily be recognized from the context by the skilled person.

A new assay for sensitive indication of tumour cell activity useful in the management of patients with carcinomas of epithelial origin, especially non-small cell lung carcinoma was therefore developed by the present inventors. An enzyme-linked immunosorbent assay (ELISA) format was chosen herein, but the skilled person will recognize that alternative formats utilizing the principles of the method according to the invention are also within the scope of the present invention.

In one embodiment of the present invention, where the three cytokeratines 8, 18 and 19 are detected, a requirement for use of monoclonal antibodies is maintained specificity for cytokeratin 19 as compared to the existing immunoradiometric assay and also good clinical correlation with the existing assay. The assay must also be stable and have acceptable signal strength.

This embodiment is advantageous in that the detection of cytokeratin 19 has been shown to be clinically superior in NSCLC. To increase sensitivity and taking into account that cytokeratins form heterodimers and that certain antibody epitopes only are available on the dimeric form, an assay was constructed for detection of cytokeratins 8, 18 and 19.

Surprisingly, a very good clinical correlation with the prior art assay could be achieved in this embodiment by combining a first labelled antibody with affinity for a dimer of cytokeratin 8 and 18 with a second labelled antibody with affinity for cytokeratin 19. The first labelled antibody should show substantially no affinity to monomers or homodimers of cytokeratin 8 or 18.

Thus, this embodiment of the method of the invention utilizes a first, second and third antibody bound to a solid phase, such as a standard microtitre plate. The first, second and third antibody immobilized to the solid phase may be produced as disclosed e.g. in WO92/05197, using purified fragments of cytokeratin 8, 18 and 19, respectively. An antibody denoted 6D7, specific for cytokeratin 8, and an antibody denoted 3F3, specific for cytokeratin 18, have been produced by this method as described in Silén et al., Scand J Clin Invest, 1995, 55, 153-161 and Stigbrand et al., Tumor Biol 1998, 19, 132-152. The antibody IDLC4 is specific for an epitope of cytokeratin 19 in the region of amino acid residues 340-370, (as set forth in SEQ ID NO:5). as discussed in Brattstrom et al., Diseases of the esophagus, 2005, 18, 298-303.

The first labelled antibody having an affinity for a dimer of cytokeratin 8 and 18 may be produced with the method according to Rydlander et al., Eur J Biochem, 1996, 241, 309-315 and screened for affinity to a dimer of cytokeratin 8 and 18 and lack of affinity to monomeric forms of cytokeratin 8 and 18. This is further explained in Example 2 below, where a suitable antibody named M21 is produced. Alternatively, the first labelled antibody may be a commercially available antibody such as A45-B/B3 (Biologicals Ltd., U.K.) or DE-K18 (Fisher Scientific).

The cell line producing 6D7 has been deposited with the European Collection of Cell Cultures (ECACC, Porton Down, United Kingdom) on 19 Mar. 2013 under accession number 13031902. The cell line producing 3F3 6D7 has been deposited with the ECACC on 19 Mar. 2013 under accession number 13031901. The cell line producing IDLC4 has been deposited with the ECACC on 19 Mar. 2013 under accession number 13031903. The cell line producing M21 has been deposited with the ECACC on 21 Mar. 2013 under accession number 13032101

The second labelled antibody used in this embodiment of the method according to the invention having affinity for cytokeratin 19 may be any antibody with affinity to cytokeratin 19 such as a commercially available antibody, e.g. A53-B/A2 (Ventana, Tuscon Ariz., U.S.A.).

In another embodiment of the method according to the invention cytokeratin 8 and 18, and/or soluble fragments thereof, in a sample are detected. More specifically, this embodiment of the method comprises the steps of
contacting said sample with a solid phase having immobilized thereon a first antibody having specificity for cytokeratin 8, and a second antibody having specificity for cytokeratin 18;
allowing cytokeratin and/or soluble fragments thereof in said sample to bind to said first and second antibodies thereby forming complexes;
contacting said complexes with a first labelled antibody having specificity for a dimer of cytokeratin 8 and 18;
allowing said labelled antibodies to bind to said complexes; and
detecting said labelled antibody bound to said complexes.

The details above relating e.g. to antibodies, their manufacture etc of the first embodiment are also applicable to this embodiment.

The above-described two embodiments, and other embodiments of the method according to the invention, are advantageously performed as one step enzyme-linked sandwich immunoassays (ELISAs). Standards, controls and samples react during incubation simultaneously with monoclonal catcher antibodies immobilized on a solid phase and Horse Radish Peroxidase (HRP)-conjugated detector antibodies. After washing, a developer substrate, e.g. 3,3',5,5'-Tetramethylbenzidine (TMB), is added and after an incubation time the reaction is stopped and the absorbance at 450 nm is measured. The developed color is directly proportional to the concentration of the analyte.

In one embodiment, an assay according to the present invention is performed with serum samples. Enough blood should be collected to be sufficient for 2×100 μl serum (duplicates) at each analysis. If the analysis is performed within 24 h, the serum should be stored refrigerated (2-8° C.). If delayed analysis, the serum is preferably stored frozen <−18° C. Repeated thawing and freezing should be avoided. Serum samples that are highly hemolysed, grossly lipemic or contaminated should not be used.

The assay procedure is schematically shown in FIG. 1.
1. Pipette 100 μl standards, controls or samples per defined well. Leave two empty wells (blank) for background absorbance measurement (optional).
2. Add 100 μl first and second labelled antibody in each well except the blank wells.
3. Incubate for 2 h±10 min on a shaker at 450 rpm.
4. Aspirate and wash the wells 3 times with 0.3 ml wash solution.
5. Add 200 μl TMB substrate per well, including the blank wells.
6. Incubate in darkness for 15±1 min.
7. Add 100 μl Stop Solution per well. Agitate on a shaker for 1 min.
8. Read the absorbance at 450 nm within 30 min after addition of the Stop Solution.

Calculate the cytokeratin 8/18/19 concentration of the samples. Samples should be diluted as appropriate, as easily determined by the skilled person, with diluent before repeated analysis.

The absorbance at 450 nm is read using a standard microplate reader (wavelength 450 nm). Computer software is used for handling the raw data. Spline smoothed is recommended as a curve fitting algorithm. For generation of valid data, it should be ensured that included controls are within range.

Manual processing of results: Correct each OD-value (optical density) by subtracting the blank OD. Calculate the mean OD-value for each duplicate. Construct a standard curve by plotting the mean OD-value for each standard (y-axis) against the corresponding concentration (x-axis). Determine the concentrations of the samples against the standard curve.

In an alternative embodiment, the method according to the present invention is performed on a urine sample in order to detect bladder cancer. Based on the information in this application and common general knowledge, the skilled person is able to prepare such a sample in the appropriate way for the detection according to the invention.

The invention further relates to a kit of parts for performing the method described above. Such a kit may advantageously comprise
a solid phase having immobilized thereon a first antibody having affinity for cytokeratin 8, and/or a second antibody having affinity for cytokeratin, 18 and/or a third antibody having affinity for cytokeratin 19; and
a first labelled antibody having affinity for a dimer of cytokeratin 8 and 18 and/or a second labelled antibody having affinity for cytokeratin 19.

The labelled antibodies are preferably provided in one or more buffered solutions. The labelled antibodies are in one embodiment labelled by conjugation to Horse Radish Peroxidase.

The kit may also comprise means for diluting samples, e.g. a ready made protein stabilized buffer of pH 7.5 which may or may not further comprise preservatives, or a dry mix for preparing such buffer when mixed with water.

The kit may further comprise means for use as standards, e.g. standard materials in protein stabilized buffer or a dry mix for preparing such buffer when mixed with water. The standards may be provided in several different concentrations.

The kit may further comprise means for use as controls, e.g. control materials in protein stabilized buffer or a dry mix for preparing such buffer when mixed with water. The standards may be provided in several different concentrations, e.g. low and high.

The kit may further comprise means for washing the solid phase (cf. step 4 in FIG. 1). The washing means may be provided as a ready-made washing solution or as a wash tablet for dissolving in water.

The kit according to the invention may also comprise written instructions for the detection of lung cancer, preferably non-small cell lung cancer; or for the detection of bladder cancer.

Although the presently preferred format for the assay according to the invention is Enzyme-Linked ImmunoSorbent Assay (ELISA), other immunoassay principles may be used to put the invention to practice. Such immunoassay principles include i.a. radioimmunoassays, fluorescence immunoassays, luminiscent oxygen channeling assay (LOCI), Surface Plasmon Resonance (SPR), ellipsometry, luminescence immunoassay (luciferase/ATP), chemiluminiscence immunoassays (dioxetane, acridinium, acridinium esters, luminol, isoluminol), electrochemiluminiscence immunoassay (ruthenium salts), dissociation enhancement time-resolved fluoroimmunoassay (DELFIA), electrical detection (conductance, carbon nanotube, semiconductor nanowires, silicone-nanowires), and Luminex (laser fluorophore).

The present invention is not limited to the above-described preferred embodiments. Various alternatives, modifications and equivalents may be used. Therefore, the above embodiments or the illustrative examples below should not be taken as limiting the scope of the invention, which is defined by the appended claims.

When practicing the present invention the person skilled in the art may further make of use conventional techniques in the field of pharmaceutical chemistry, immunology, molecular biology, microbiology, cell biology, and recombinant DNA technology, as i.a. disclosed in Sambrook et al. "Molecular cloning: A laboratory manual", $3^{rd}$ ed. 2001; Ausubel et al. "Short protocols in molecular biology", $5^{th}$ ed. 1995; "Methods in enzymology", Academic Press, Inc.; MacPherson, Hames and Taylor (eds.). "PCR 2: A practical approach", 1995; "Harlow and Lane (eds.) "Antibodies, a laboratory manual" 1988; Freshney (ed.) "Culture of animal cells", $4^{th}$ ed. 2000; "Methods in Molecular Biology" vol. 149 ("The ELISA Guidebook" by John Crowther) Humana Press 2001, or later editions of these books.

EXPERIMENTAL PART

The examples below are provided for illustrative purposes only, and should not be construed as limiting the invention which is defined by the appended claims. All references provided below and elsewhere in the present application are hereby included herein by reference.

Example 1

In order to find a suitable monoclonal detector antibody for conjugation in the ELISA format a number of monoclonal antibodies were evaluated. Interaction between cytokeratins 8, 18 and 19 bound to catcher antibodies (3F3, 6D7 and IDLC4) were evaluated in real time using a Quartz Crystal Microbalance biosensor instrument from Attana AB (Stockholm, Sweden), providing information on binding strength, on-rate, binding level and binding stability and epitope similarity.

Six antibodies with affinity for cytokeratin 19, three with affinity for cytokeratin 8, four with affinity for cytokeratin 18 and one with affinity for a number of cytokeratins were evaluated, cf. Table 1.

TABLE 1

| Anti CK 19 | Anti CK 8 | Anti CK 18 | Pan ab |
|---|---|---|---|
| IDL C3 | IDL33 | 3F3 | C11 |
| IDL C4 | 6D7 | M3 | |
| IDL C5 | 2D1 | M21 | |
| A53-B/A2 | | M34 | |
| BA 17 | | | |
| HCA 077 | | | |

Based on results from the biosensor tests, antibodies A53-B/A2, IDL33, HCA 077, M21 and C11 were conjugated to HRP and tested in enzyme-linked immunosorbent assays and evaluated for clinical correlation with the prior art assay.

12 samples or pooled samples from cancer patients diluted 1:2 or 1:4 in MonoTotal diluent were used for comparison. The conjugated antibodies or mixes of antibodies were diluted to a final concentration of 1 µg/ml. A standard of 5472 U/l diluted 1:2 in six steps were used.

Protocol:
100 µl standard/sample/diluted sample
100 µl conjugated antibody
2 hours shaking 450 rpm
Wash 2*3*300 µl
200 µl TMB
15 min incubation in the dark
100 µl stop solution
1 min shaking
Reader: 450 nm.

Results

The concentrations for the various assay variants were generated in Gen5 and plotted versus MonoTotal IRMA data, whereafter a linear fit was made in MS Excel. The results are summarised in Table 2.

TABLE 2

| Conjugate | $R^2$ |
|---|---|
| C11 | 0.8023 |
| M21 | 0.9231 |
| A53-B/A2 | 0.9395 |
| HCA 077 | 0.8435 |
| C11 + M21 | 0.9357 |
| C11 + A53-B/A2 | 0.9579 |
| C11 + HCA 077 | 0.9339 |
| M21 + A53-B/A2 | 0.9936 |
| M21 + HCA 077 | 0.8615 |
| A53-B/A2 + HCA 077 | 0.9479 |

Surprisingly, a very good clinical correlation ($R^2$=0.9936) with the prior art assay could be achieved by combining a monoclonal antibody (M21) with affinity for cytokeratin 18 but without known affinity for cytokeratin 8, with a monoclonal antibody with affinity for cytokeratin 19 (A53-B/A2).

Example 2

This example shows that the antibody M21 as used in Example 1 binds to a heterodimer of cytokeratins 8 and 18, but not to pure cytokeratin 18. M21 has previously been shown to bind to cytokeratin 18, see Rydlander et al, Eur. J.

Biochem. 1996, 241, 3009-314, but it has not been shown that this binding requires that the cytokeratin 18 is bound to cytokeratin 8.

Example 2.1

Avidin strips were coated with biotin coupled antibodies M21, M34 and 3F3 in room temperature and washed with 3*300 µl wash solution. The coated strips were incubated with a standard solution of culture supernatant from a tumor cell line containing cytokeratin fragments from cytoskeleton, mainly cytokeratins 8, 18 and 19, in concentrations 0, 120 and 1200 U/l or a reference solution of pure recombinant cytokeratin 18 in dilutions 1:1, 1:2, 1:4, 1:8. Bound cytokeratin 18 were detected by HRP-conjugated monoclonal antibody M3 or polyclonal horse anti-TPS antibody P03.

The results are summarized in Table 3 and shown in FIG. 2A-D.

TABLE 3

|  | M34 | 3F3 | M21 |
|---|---|---|---|
| HRP-conjugated M3 | | | |
| Blank | 0.059 | 0.058 | 0.056 |
| Std 0 | 0.057 | 0.059 | 0.056 |
| Std 120 | 0.058 | 0.061 | 0.19 |
| Std 1200 | 0.098 | 0.065 | 1.342 |
| CK18 ref | 0.828 | 0.058 | 0.062 |
| 1:2 | 0.411 | 0.063 | 0.072 |
| 1:4 | 0.227 | 0.059 | 0.062 |
| 1:8 | 0.145 | 0.066 | 0.065 |
| HRP-conjugated P03 | | | |
| Blank | 0.062 | 0.059 | 0.056 |
| Std 0 | 0.139 | 0.133 | 0.172 |
| Std 120 | 0.152 | 0.265 | 0.344 |
| Std 1200 | 0.181 | 1.451 | 1.047 |
| CK18 ref | 0.637 | 0.717 | 0.218 |
| 1:2 | 0.341 | 0.375 | 0.259 |
| 1:4 | 0.239 | 0.233 | 0.199 |
| 1:8 | 0.184 | 0.197 | 0.173 |

The results clearly indicate that the antibody M21 essentially lack affinity for pure recombinant cytokeratin 18, but has affinity to a mixture of cytokeratins 8, 18 and 19.

Example 2.2

Stock Solutions of Antibody M21 (0.65 mg/ml) and M34 (0.58 mg/ml) were prepared

The wells of a 96-well microtitre plate for ELISA were coated with M21 antibody and a mixture of M21 and M34 antibody in six different variants:
Reference: TPS standard (polyclonal horse anti-TPS)
Variant 1: 12 µg/ml M21+0.5 mg/ml Bovine Serum Albumin
Variant 2: 16 µg/ml M21+0.5 mg/ml BSA
Variant 3: 20 µg/ml M21+0.5 mg/ml BSA
Variant 4: 12 µg/ml M21+4 µg/ml M34
Variant 5: 16 µg/ml M21+4 µg/ml M34
Variant 6: 20 µg/ml M21+4 µg/ml M34

To each variant was added 50 µl cancer sample (pooled samples from Breast Cancer (BC) patients), normal sample (from healthy Blood Donors (BD)), TPS (tissue-polypeptide specific antigen) diluent (0 U/l) or TPS standard (1200 U/l) (IDL Biotech, Bromma, Sweden), recombinant cytokeratin 18, or a mixture of recombinant cytokeratin 8 and 18. 50 µl HRP-conjugated mAb M3 200 ng/ml was added, the wells were incubated on a shaker in room temperature for 2 hours at ~450 rpm and then washed three times with 300 µl wash solution. 200 µl TMB substrate was added and the wells were incubated 20 minutes in the dark. 50 µl stop solution was added and the wells were shaken for 1 minute. Bound cytokeratins was detected by measuring the absorbance at 450 nm.

Figure 3:
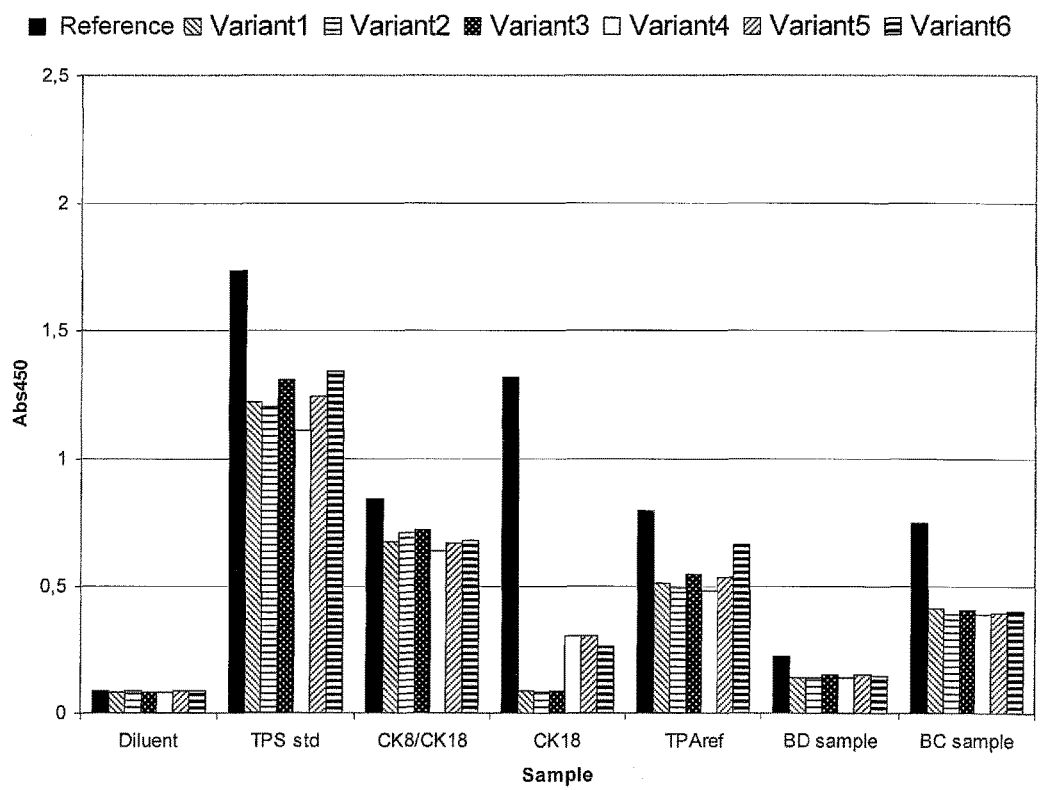
FIG. 3 is a diagram showing the results obtained in example 2.2.

The results are shown in table 4 and FIG. 3.

TABLE 4

|  | Reference | Variant1 | Variant2 | Variant3 | Variant4 | Variant5 | Variant6 |
|---|---|---|---|---|---|---|---|
| Diluent | 0.089 | 0.082 | 0.087 | 0.084 | 0.084 | 0.087 | 0.088 |
| TPS std | 1.736 | 1.218 | 1.201 | 1.307 | 1.109 | 1.243 | 1.341 |
| CK8/CK18 | 0.839 | 0.671 | 0.71 | 0.717 | 0.636 | 0.669 | 0.681 |
| CK18 | 1.317 | 0.086 | 0.084 | 0.088 | 0.299 | 0.301 | 0.259 |
| TPAref | 0.793 | 0.513 | 0.494 | 0.544 | 0.48 | 0.536 | 0.66 |
| BD sample | 0.22 | 0.14 | 0.141 | 0.152 | 0.141 | 0.15 | 0.147 |
| BC sample | 0.749 | 0.41 | 0.391 | 0.404 | 0.391 | 0.397 | 0.402 |

The results show that M21 alone shows affinity for the combination of cytokeratins 8 and 18, but not for pure cytokeratin 18.

Analogous experiments will show that M21 does not show affinity for pure cytokeratin 8, i.e. cytokeratin 8 in the absence of cytokeratin 18.

Example 3

This example shows that an advantageous assay format may be provided by replacing the polyclonal antibody from horse used in the prior art (UBC/TPAcyk) with two monoclonal antibodies, which are specific to cytokeratin 8 (CK8) and cytokeratin 18 (CK18).

The antibodies were first tested for epitope similarity and kinetics in an instrument from Attana A100 QCM Research System (website attana.com). The test was performed on polystyrene chips coated with antibody 6D7/3F3 in proportions equivalent to an ELISA test. The antibodies that worked satisfactorily were conjugated and for further tests in ELISA.

The conjugates in the table below are of the concentration 1 µg/ml. The binding (ABS) of the highest standard is reported.

| Ab | Specificity | Attana result | UBC ELISA |
|---|---|---|---|
| IDL33 | CK 8 | Very low binding | UBC std. 15 µg/l = 0.25 |
| 2D1 | CK 8 | High binding High off-rate | UBC std. 15 µg/l = 0.17 |
| M21 | CK 18 | High binding Higher on-rate and lower off-rate compared to 2D1 Binding is partly inhibited by 2D1 | UBC std. 15 µg/l = 0.73 UBC std. 15 µg/l = 0.64 Std1 < blg < std 2 UBC std. 15 µg/l = 0.65 |
| M3 | CK 18 | Medium binding Low off-rate Binding is partly inhibited by all antibodies except 2D1 | UBC std. 15 µg/l = 0.52 |
| C11 | Pan ak Bl.a. CK 8 and 18 | High binding Slower on-rate compared to M21 Low off-rate No inhibition from the other antibodies | UBC std. 15 µg/l = 1.37 UBC std. 15 µg/l = 1.48 Std0 < blg < std 1 UBC std. 15 µg/l = 1.50 |

UBC ELISA with Different Conjugates

The plate was coated with equal parts of 6D7 (anti CK8) and 3F3 (anti CK18), the standard is comprised of equal parts of recombinant CK8 and CK18. Tests were performed with internal controls and patient samples.

| Conjugate (1 µg/ml) | Binding to std. 0 and 15 µg/l (ABS) | Correlation to the prior art assay | Correlation coefficient ($r^2$) | Number of samples |
| --- | --- | --- | --- | --- |
| C11 | 0.050/1.5 | y = 6.7x − 0.1 | 0.80 | 27 |
| C11 + M21 | 0.060/1.6 | y = 1.2x + 0.2 | 0.92 | 27 |
| M21 | 0.065/0.7 | y = 1.3x + 0.8 | 0.91 | 12 |
| C11 + M21 | 0.055/1.9 | y = 1.6x + 1 | 0.94 | 12 |

As appears from above, C11 works well, it bound after all antibodies investigated, and has an epitope on both CK8 and CK18.

M21 alone gives a good correlation to the prior art assay but very low binding.

The combination of C11+M21 provides a binding which is roughly equivalent to C11 alone. The combination provides good binding and good correlation. The combination also allows a lower concentration of C11, and may be an advantageous economic alternative.

CONCLUSION

This example shows that the combination of C11 with M21 is a fully operable alternative to the prior art assay.

The invention claimed is:

1. A method for detecting at least two cytokeratins selected from the group consisting of cytokeratin 8, 18 and 19 in a sample, comprising the steps of
   contacting said sample with a solid phase having immobilized thereon a first antibody having specificity for cytokeratin 8, a second antibody having specificity for cytokeratin 18 and optionally a third antibody having specificity for a first epitope of cytokeratin 19;
   allowing cytokeratins in said sample to bind to said first, second and optionally third antibodies thereby forming complexes;
   contacting said complexes with a first labelled antibody having specificity for a dimer of cytokeratin 8 and 18 and optionally a second labelled antibody having specificity for a second epitope of cytokeratin 19;
   allowing said labelled antibodies to bind to said complexes; and
   detecting said labelled antibodies bound to said complexes.

2. The method according to claim 1, wherein said antibodies are monoclonal antibodies.

3. The method according to claim 1 or 2, wherein said first labelled antibody has specificity for the α-helix 2B 2 (aa 414-429 as set forth in SEQ ID NO:1) of cytokeratin 18, and, if present, said second labelled antibody has specificity for the α-helix 2B 2 (aa 311-335 as set forth in SEQ ID NO:2) of cytokeratin 19.

4. The method according to claim 3, wherein said first labelled antibody is M21, and, if present, said second labelled antibody is A53-B/A2.

5. The method according to claim 1, wherein said first immobilized antibody has specificity for the α-helix 2B (aa 340-365 as set forth in SEQ ID NO:3), said second immobilized antibody has specificity for the α-helix 2B (aa 320-350 as set forth in SEQ ID NO:4), and, if present, said third immobilized antibody has specificity for the α-helix 2B (aa 340-370 as set forth in SEQ ID NO:5).

6. The method according to claim 5, wherein said first immobilized antibody is 6D7, said second immobilized antibody is 3F3, and, if present, said third immobilized antibody is IDLC4.

7. The method according to claim 1, wherein said first antibody having specificity for cytokeratin 8 constitutes 20-40% of total immobilized antibody, said second antibody having specificity for cytokeratin 18, constitutes 5-15% of total immobilized antibody, and said third antibody having specificity for cytokeratin 19 constitutes 50-70% of total immobilized antibody.

8. The method according to claim 1, wherein cytokeratin 8 and 18 in a sample are detected, comprising the steps of
   contacting said sample with a solid phase having immobilized thereon a first antibody having specificity for cytokeratin 8, and a second antibody having specificity for cytokeratin 18;
   allowing cytokeratin in said sample to bind to said first and second antibodies thereby forming complexes;
   contacting said complexes with a first labelled antibody having specificity for a dimer of cytokeratin 8 and 18;
   allowing said labelled antibodies to bind to said complexes; and
   detecting said labelled antibody bound to said complexes.

9. The method according to claim 1, wherein said labelled antibodies are labelled with horse radish peroxidase and detection is performed by adding a substrate capable of being converted to a detectable substance by said horse radish peroxidase.

10. The method according to claim 9, wherein said substrate is converted to a chromogenic substance by said horse radish peroxidase.

11. A method for quantitative determination of at least two cytokeratins selected from the group consisting of cytokeratin 8, 18 and 19 in a sample, comprising the method according to claim 1 or 8 and further comprising the step of:
    quantitatively correlating the amount of bound first labelled antibody having specificity for a dimer of cytokeratin 8 and 18 and, if present, second labelled antibody having specificity for cytokeratin 19 with known amounts of cytokeratins 8, 18 and/or 19.

12. A kit for detecting at least two cytokeratins selected from the group consisting of cytokeratin 8, 18 and 19 in a sample, comprising
    a solid phase substrate having immobilized thereon at least two cytokeratin-specific antibodies selected from the group consisting of a first antibody having specificity for cytokeratin 8, a second antibody having specificity for cytokeratin 18; and a third antibody having specificity for cytokeratin 19; and
    a first labelled antibody having specificity for a dimer of cytokeratin 8 and 18 and optionally a second labelled antibody having specificity for cytokeratin 19.

13. The kit according to claim 12, further comprising diluent means, standard means, control means, substrate means, stop means, wash means and/or instructions for use.

14. The kit according to claim 12 or 13, adapted for an Enzyme-Linked ImmunoSorbent Assay (ELISA).

15. The kit according to claim 12, wherein a first antibody having specificity for cytokeratin 8 and a second antibody having specificity for cytokeratin 18 have been immobilized to the solid substrate.

16. The kit according to claim 15, wherein said first labelled antibody is M21, and said optional second labelled antibody is C11.

17. The kit according to claim 12, which further comprises written instructions for the detection of lung cancer.

18. The kit according to claim 12, which further comprises written instructions for the detection of bladder cancer.

19. The method according to claim 7, wherein said first antibody having specificity for cytokeratin 8 constitutes 30% of total immobilized antibody, said second antibody having specificity for cytokeratin 18, constitutes 10% of total immobilized antibody, and said third antibody having specificity for cytokeratin 19 constitutes 60% of total immobilized antibody.

20. The method according to claim 10, wherein said substrate is TMB (3,3',5,5'-Tetramethylbenzidine).

21. The kit of claim 12, wherein the labeled antibodies are in a buffered solution.

22. The kit according to claim 17, wherein the lung cancer is non-small cell lung cancer.

* * * * *

SEQUENCE LISTING

```
<160> NUMBER OF SEQ ID NOS: 5

<210> SEQ ID NO 1
<211> LENGTH: 16
<212> TYPE: PRT
<213> ORGANISM: Homo sapiens

<400> SEQUENCE: 1

Val Asp Gly Lys Val Val Ser Glu Thr Asn Asp Thr Lys Val Leu Arg
1               5                   10                  15

<210> SEQ ID NO 2
<211> LENGTH: 25
<212> TYPE: PRT
<213> ORGANISM: Homo sapiens

<400> SEQUENCE: 2

Gln Ser Gln Leu Ser Met Lys Ala Ala Leu Glu Asp Thr Leu Ala Glu
1               5                   10                  15

Thr Glu Ala Arg Phe Gly Ala Gln Leu
            20                  25

<210> SEQ ID NO 3
<211> LENGTH: 26
<212> TYPE: PRT
<213> ORGANISM: Homo sapiens

<400> SEQUENCE: 3

Gln Arg Gly Glu Leu Ala Ile Lys Asp Ala Asn Ala Lys Leu Ser Glu
1               5                   10                  15

Leu Glu Ala Ala Leu Gln Arg Ala Lys Gln
            20                  25

<210> SEQ ID NO 4
<211> LENGTH: 31
<212> TYPE: PRT
<213> ORGANISM: Homo sapiens

<400> SEQUENCE: 4

Leu Glu Asn Ser Leu Arg Glu Val Glu Ala Arg Tyr Ala Leu Gln Met
1               5                   10                  15

Glu Gln Leu Asn Gly Ile Leu Leu His Leu Glu Ser Glu Leu Ala
            20                  25                  30

<210> SEQ ID NO 5
<211> LENGTH: 31
<212> TYPE: PRT
```

```
<213> ORGANISM: Homo sapiens
<220> FEATURE:
<221> NAME/KEY: VARIANT
<222> LOCATION: (12)..(12)
<223> OTHER INFORMATION: May alternatively be D
<220> FEATURE:
<221> NAME/KEY: VARIANT
<222> LOCATION: (16)..(16)
<223> OTHER INFORMATION: May alternatively be D

<400> SEQUENCE: 5

Ala Leu Ile Ser Gly Ile Glu Ala Gln Leu Ala Lys Val Arg Ala Lys
1               5                   10                  15

Ser Glu Arg Gln Asn Gln Glu Tyr Gln Arg Leu Met Asp Ile Lys
            20                  25                  30
```